United States Patent [19]

Weldon et al.

[11] 4,365,191

[45] Dec. 21, 1982

[54] METHOD AND APPARATUS FOR ELECTRICAL SURVEYS OF OFFSHORE METAL STRUCTURES WITH CORRECTION FOR DISTANCE

[75] Inventors: Clark P. Weldon; Stephen L. Wolfson; Marvin L. Miller, all of Houston, Tex.

[73] Assignee: Harco Corporation, Medina, Ohio

[21] Appl. No.: 125,885

[22] Filed: Feb. 29, 1980

[51] Int. Cl.[3] .......................... G01R 31/02; G01V 3/15
[52] U.S. Cl. .................................. 324/71 R; 324/52; 324/54; 324/348; 324/365; 364/571
[58] Field of Search ............ 324/52, 54, 65 CR, 71 R, 324/72, 330, 331, 326, 334, 348, 357, 365; 367/15, 19, 127, 130, 177; 364/561, 571

[56] References Cited

U.S. PATENT DOCUMENTS

| 2,378,440 | 6/1945 | Scott | 324/357 X |
| 2,610,226 | 9/1952 | Klaasse et al. | 324/331 |
| 3,490,032 | 1/1970 | Zurflueh | 324/331 X |
| 3,526,831 | 9/1970 | Smith | 324/326 X |
| 4,010,413 | 3/1977 | Daniel | 324/335 |
| 4,228,399 | 10/1980 | Rizzo et al. | 324/365 X |
| 4,231,111 | 10/1980 | Neeley | 367/130 X |
| 4,258,323 | 3/1981 | Andrews et al. | 324/326 X |

*Primary Examiner*—Gerard R. Strecker
*Attorney, Agent, or Firm*—Maky, Renner, Otto & Boisselle

[57] ABSTRACT

In the present invention a method and apparatus for electrical surveys of offshore metal structures includes measuring the electrical potential difference between the structure and an electrolyte, such as sea water and/or the sea bottom, in which the structure is contained. Such measurements are made at roughly approximated recorded distance locations along the structure and the approximate distance information is corrected based on periodically taken accurate distance measurements. Provision is also made to correct data for line currents in the structure, and a method is disclosed for examining the effectiveness of an electrically insulating member connected in the structure. Moreover, an improved insulated wire having minimum insulation holidays and a method for making the same are disclosed.

49 Claims, 8 Drawing Figures

IR DROPS IN PIPE-TO-ELECTROLYTE POTENTIAL

CURRENT FLOW TOWARD PIPE CONTACT

CURRENT FLOW AWAY FROM PIPE CONTACT

METHOD AND APPARATUS FOR ELECTRICAL SURVEYS OF OFFSHORE METAL STRUCTURES WITH CORRECTION FOR DISTANCE

TECHNICAL FIELD

The present invention relates generally to a method and apparatus for electrical surveys of metal structures, particularly those located in marine environments, to examining and/or testing procedures related to such structures and surveys and to an improved insulated wire for use in such surveys.

BACKGROUND OF PRIOR ART

The discussion following in this specification is directed to metal structures contained in an electrolyte and to method and apparatus to enable the surveying of such structures with a high level of accuracy and efficiency. In particular, such a structure will be described as a pipeline, but other structures may be surveyed. The electrolyte in which the pipeline is contained is described as sea water and/or sea bottom, but the electrolyte may be other environments, including, for example, soil that is not necessarily submerged. The survey itself is affected by measuring the electrical potential difference between the pipeline and the electrolyte existing at distance locations along the pipeline; however, it is contemplated that other types of electrical measurements may be made in connection with such surveys. The data obtained in such surveys may be used as an indication of the condition of the pipeline, the probability that a corrosion problem will occur at a given location on the pipeline, the effectiveness of cathodic protection apparatus associated with the pipeline, etc.

In view of the very corrosive environment in which offshore pipelines are installed, cathodic protection is generally required. Monitoring of the level of cathodic protection is an essential component of maintaining effective corrosion control; data from surveys in which a series of electrical measurements are taken indicate whether the installed cathodic protection equipment is functioning properly. The surveys may be made of pipelines with galvanic cathodic protection or impressed current cathodic protection.

In the past, to examine or to determine the level or effectiveness of cathodic protection of an onshore buried pipeline, pipe-to-soil potentials were measured at intervals along the length of the line. The intervals were selected to provide a representative profile of the potentials along the entire length of the line. One example of an apparatus and method for making such a survey is presented in U.S. Pat. No. 4,151,458, which is assigned to the assignee of the present application.

Another example of apparatus and method of the computerized type for making such surveys, either onshore or offshore, is presented in U.S. patent application Ser. No. 17,180, filed Mar. 5, 1979, now U.S. Pat. No. 4,322,805 which application is assigned to the assignee of the present application. Still another example of apparatus and method directed particularly to an offshore pipeline electrical survey is disclosed in U.S. patent application Ser. No. 881,737, filed Feb. 27, 1978, now U.S. Pat. No. 4,228,399 which also is assigned to the assignee of the present application.

The disclosures of the above-mentioned patent and applications are hereby incorporated by reference. Also, as used here marine and offshore are equivalent and interchangeable.

Very generally, the survey techniques disclosed in such patent and applications broadly include the connecting of a wire to a test station, which is electrically connected to the pipeline, moving an electrode to certain locations along the pipeline to make contact with the electrolyte in which the pipeline is contained, measuring the electrical potential difference between the electrolyte via the electrode and the pipeline via the wire, and correlating the potential difference data with the distance locations along the pipeline at which such electrical measurements are made and data taken.

It will be appreciated that the task of acquiring a complete potential profile on an offshore pipeline may be more difficult than is the case for an onshore pipeline. In offshore surveys the distance between test stations frequently exceeds 20 miles; whereas adjacent test stations for onshore pipelines ordinarily are much closer. Thus, the strength of the wire used in an offshore survey must be adequate to avoid breakage when streamed out over the relatively long distances encountered, and the accuracy of data collecting and measuring and of distance measuring must be relatively high. Moreover, preferably the wire should be reasonably light weight and gauge for optimum facility of usage and storage and for minimum cost. Additionally, the insulation on the wire used in offshore surveys should have a minimum of holidays or areas in the insulation to which water may find easy access to the conductor which would have a detrimental effect on potential difference measurement; on the other hand, in onshore surveys the criticality of insulation integrity is not as severe. Furthermore, in the offshore survey the wire should be economically disposable and should be of a size, weight and strength such that even if the wire were dropped or disposed of in place at the conclusion of a survey without picking up the wire, such in place disposal would not have a significant effect on the environment.

It is often desirable to provide electrical insulation between that portion of a pipeline ordinarily submerged and that portion extending onshore or onto a platform to prevent stray signals from entering the submerged pipeline and to optimize the effectiveness of the cathodic protection system for the pipeline. However, sometimes the effectiveness of an insulating member in the pipeline may be reduced or totally lost, e.g. short circuited, and, therefore, it is desirable to enable a facile technique for examining the effectiveness of such insulating members. In other instances line currents, i.e. currents flowing in the pipeline, are intended, but such line currents may detrimentally affect the accuracy of potential difference measurements and the complete potential profile of a pipeline. Thus, it would be desirable to correct data taken in such surveys to eliminate or to overcome the effect of line currents on such measurements.

Another difficulty in offshore surveys is maintaining accurate distance information, vis-a-vis the locations along the pipeline at which potential difference measurements are taken. The wire may drift, for it is undesirable to maintain tight tension on the wire which might unnecessarily cause a breakage. With the wire being used not only for electrical connecting purposes but also for distance measuring purposes, for example as is disclosed in the above mentioned patent and application, such drifting and/or sinking of the wire will cause inaccuracies in the distance measurement data; such inaccuracies generally are avoided in onshore surveys because there is no drifting or sinking and due to the relatively close proximity of adjacent test stations. Thus, it would be desirable to maintain the accuracy of distance information obtained in offshore surveys.

BRIEF SUMMARY OF INVENTION

With the foregoing in mind, it is a principal object of the present invention to facilitate surveying structures in an electrolyte, especially offshore structures.

Another object is to correlate the electric potential difference measurements taken in such surveys accurately with position along the structure.

An additional object is to improve the quantity, quality and accuracy of data taken in such surveys, and especially to achieve the same while facilitating the survey.

A further object is to detect during such surveys line currents in the surveyed structure, and, furthermore, to compensate for same.

Still another object is to examine the effectiveness of an insulating member in a metal structure at least part of which is contained in an electrolyte.

Still an additional object is to minimize the number of holidays in an insulated wire.

Still a further object is to provide a relatively strong, conveniently usable, preferably economically disposable wire for use in such surveys.

These and other objects and advantages of the present invention will become more apparent as the following description proceeds.

In accordance with one aspect of the invention a method of surveying a structure in an electrolyte includes sensing at locations along the structure the electrical potential difference between the structure and the electrolyte, measuring the approximate distances along the structure of a plurality of such locations, making an accurate measurement of distance along the structure, and correcting such approximate distances based on information from such accurate distance measurements. In accordance with another aspect of the invention an apparatus for practicing the just-summarized method is provided.

In accordance with another aspect of the invention, a method of surveying a structure in an electrolyte includes sensing seriatim in one direction at locations along the structure the electrical potential difference between the structure and the electrolyte, sensing seriatim in the opposite direction at locations along the structure the electrical potential difference between the structure and the electrolyte, and comparing the data obtained in said respective sensing steps to detect whether the structure was carrying line current during at least one of said sensing steps. In accordance with another aspect of the invention an apparatus for practicing the just-summarized method is provided.

In accordance with another aspect of the invention, a method of surveying a structure in an electrolyte includes sensing at locations along the structure the electrical potential difference between the structure and the electrolyte, determining whether such structure is carrying line current, and correcting such electrical potential difference information obtained in said sensing step based on such line current. In accordance with another aspect of the invention an apparatus for practicing the just-summarized method is provided.

In accordance with another aspect of the invention, a method of examining the effectiveness of an electrically insulating member connected in a structure which has a portion contained in an electrolyte includes measuring structure to electrolyte potential difference with contact at one side of such member, measuring structure to electrolyte potential difference with contact at the other side of such member, and comparing such potential differences, whereby a difference indicates effective insulation by such member and no difference indicates a high probability of lack of insulating effectiveness of such member. In accordance with another aspect of the invention an apparatus for practicing the just-summarized method is provided.

In accordance with another aspect of the invention a wire having minimum insulation holidays comprises an elongate conductor and an insulating coating of polymer material, and, in accordance with another aspect, a further insulating coating of film-like material is provided between the conductor and polymer coating. Moreover, in accordance with still another aspect of the invention, a method of making such wire also is provided.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

DETAILED DESCRIPTION OF INVENTION

Figure 1:
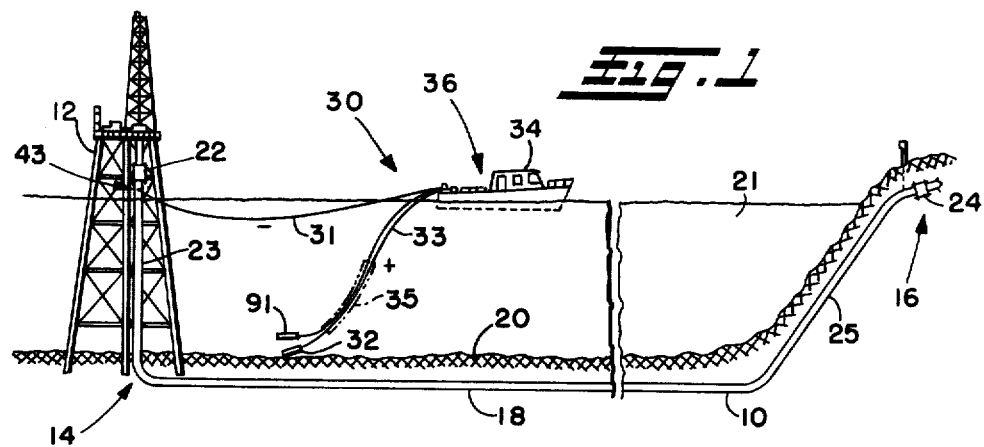
FIG. 1 is a schematic illustration showing the manner in which the broad concept of the invention may be practiced.

Referring now in greater detail to the drawings, and initially to FIG. 1, a typical marine pipeline 10, or other elongate structure, usually made of metal, extends between an offshore platform 12 at one end 14 and a remote onshore connection, such as a pump, a tank, or other apparatus, at the other end 16. A major portion 18 of the pipeline 10 rests on the sea bed 20 or is partially buried ordinarily from 2 to 10 feet therein, such major portion, then, being considered a marine pipeline contained within an electrolyte, namely the sea bed 20 and/or the sea water 21. The major portion 18 of the pipeline 10 preferably is provided with one of the various types of cathodic protection systems (not shown). An electrically insulating flange-like member 22 is connected at the one end 14 of the pipeline 10 near the top of the pipeline riser 23 to provide a continuous flow through coupling of the pipeline portions which are in fluid-tight coupling relations with opposite sides of the flange 22. When used the flange 22 electrically insulates or isolates the major portion 18 of the pipeline 10 from that pipeline portion at the platform 12 which ordinarily is not expected to become submerged in the sea water 21 thereby to isolate electrically between those pipeline portions on opposite sides of the flange 22. A similar insulating flange 24 also may be provided in the pipeline riser 25, if desired, to provide the same function as the flange 22.

The apparatus for practicing the methods of the invention is generally designated 30. Such apparatus 30 is intended to obtain data concerning the electrical potential difference between the pipeline, to which an electrical connection is made via a wire 31, and the electrolyte (used herein to refer to the sea bed 20 and/or the sea water 21), to which electrical connection effectively is made via a reference electrode 32 electrically connected via a wire 33 in the apparatus 30. Such potential difference data is obtained at plural locations along the pipeline 10 by moving the reference electrode 32 along the major portion 18, for example, by towing such electrode, if desired mounted on a support, by a boat 34 using a cable 35 within which the wire 33 may be incorporated. Thus, another function of the apparatus 30 is to acquire data indicative of the various locations at which such potential difference data is measured in a manner such that the potential difference and distance data can be correlated to generate a substantially continuous potential profile of the major portion 18 of the pipeline 10.

The reference electrode 32 may be a conventional silver-silver chloride half cell weighted to pass proximate the pipeline 10, ideally just above the pipeline or mud/water interface above the pipeline in those instances where the pipeline is buried. The boat 34 also carries electrical equipment 36 which measures the electrical potential difference between the pipeline and electrolyte via signals received on wires 31, 33. The electrical equipment 36 also includes a means for roughly approximating the distance of the boat 34 and, thus, the reference electrode 32 from the test station connection of the wire 31 to the one end 14 of the pipeline 10 at the pipeline riser 23, with such distance measurement preferably being made by measuring the length of wire 31 payed out from a wire supply carried on the boat 34; and a means for accurately measuring the location of the boat 34 (and, thus, the electrode 32) or the distance of the same along the pipeline 10.

Figure 2:
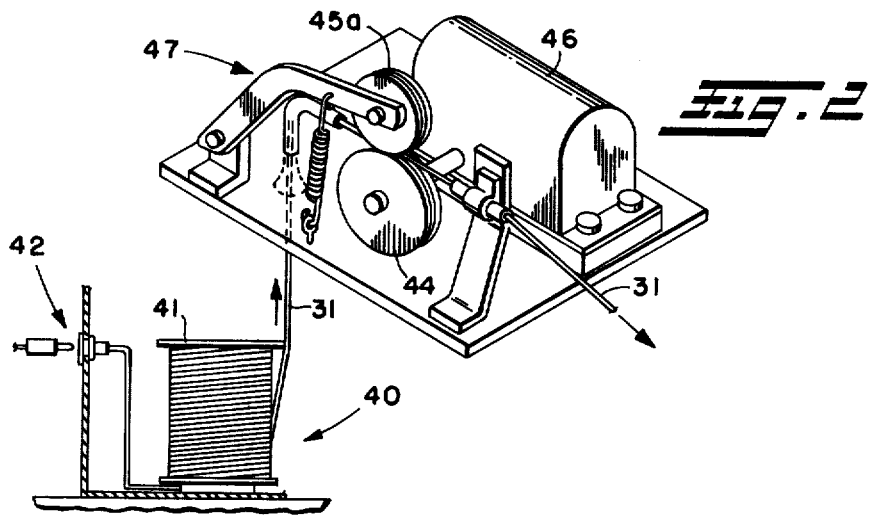
FIG. 2 is a schematic illustration of a wire dispenser and length/distance measuring apparatus.

Turning now to FIG. 2, a supply 40 of wire 31 is stored on a reel 41 supported on a boat 34. The wire 31 is electrically connected, for example by a connection generally indicated at 42, to the electrical equipment 36 to provide a signal to the latter representative of that delivered from the pipeline via the connection 43 at the pipeline riser 23 (FIG. 1). As the boat 34 traverses or travels along the pipeline 10, with the mechanical and electrical connection of wire 31 being made at the connection 43, wire 31 is drawn from the supply 40 on reel 41 over a roller or pulley 44 and through a glass tube out-feed guide 45 allowing an increase in the length of the wire 31 between the connection 43 and the boat 34. A spring loaded idler roller 45a holds the wire 31 against the pulley 44 so that as wire is payed out through the guide 45, the wire will turn the pulley 44. The turning pulley 44 drives a counter/transducer mechanism 46 which produces a mechanical and/or electrical output indicative of the length of wire 31 payed out from the just-described wire dispenser/pay out assembly 47. It is intended that the assembly 47 cause a minimum of tension on the wire 31 payed out therefrom, provide to the electrical equipment 36 via connection 42 the electrical potential signal from line 31, provide to the electrical equipment 36 via an electrical connection 50, such as a cable, (FIG. 3) an electrical signal representing the length of wire payed out and, thus, the approximate distance of the boat 34 from the connection 43, and facilitate changing reels to substitute a fresh wire supply 40 for a depleted supply. Various portions of the assembly 47 may be similar in construction and operation to those disclosed in the aforesaid patent and application.

Figure 3:
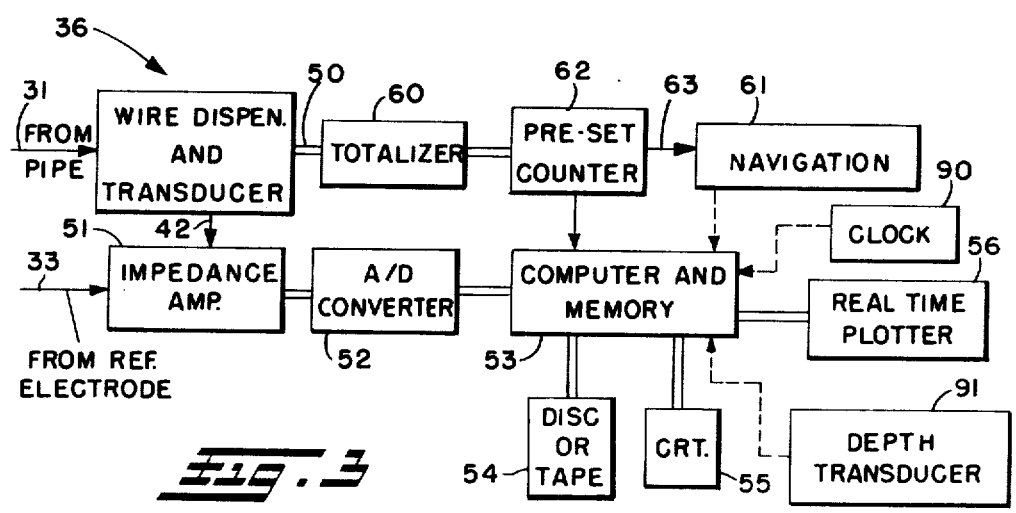
FIG. 3 is a block diagram depicting the cooperative interrelations between various portions of the invention.

Referring now to FIG. 3, the various components of the electrical equipment 36 are shown in detail. The wire 31 is connected via the dispenser assembly 47 and connection 42 to the negative input terminal of the equipment 36 and in particular to an input of an adjustable impedance amplifier 51, the impedance of which may be adjusted, for example, over a range of about 2 megohms to about 200 megohms. The positive terminal of the electrical equipment 36, namely at an input of the amplifier 51 is connected via the wire 33 to the reference electrode suspended from and trailing behind the boat 34 as it moves along the pipeline 10. For exemplary purposes in the following discussion it will be assumed that the electrode 32 is directly below the boat 34; in practice, though, the electrode 32 will trail behind the boat, but that trailing distance may be measured and used for appropriate distance data correction in conventional manner in completing the potential profile for the pipeline.

Electronic equipment included in the electrical equipment 36 for measuring, monitoring and recording the electrical potential difference information includes an analog to digital converter (A/D) 52, and a computer 53 with suitable internal memory. The A/D 52 converts the potential difference information received from the amplifier 51 to digital information which is delivered to the computer 53. The computer may operate on the potential difference information, and the computer then delivers potential difference data to peripheral equipment, such as a disc drive 54 in which data is stored on a floppy disc or a tape drive with magnetic tape, etc., a cathode ray tube display 55 for visual data display either in discrete numerical and/or graphical form, and a real time plotter 56 which constructs a graph of the pipe to electrolyte potential difference data versus distance, i.e. pipeline location at which data is taken. The amplifier 51 may be a conventional one with selective adjustments provided for the impedance thereof. The A/D may be a conventional one operative independently or preferably under control of the computer 53, and the latter may be an Altair Model 8800 DM microcomputer. The disc drive 54 may be a conventional one, and the cathode ray tube 55 and plotter 56 may be, respectively, a model ADM cathode ray tube of Lear Siegler, Inc. and a Hewlett Packard Model 7221-A graphics plotter. Identification of parts herein is exemplary only in accordance with the preferred embodiment and the best mode of the invention; however, equivalent products may be substituted, as will be well appreciated by those having ordinary skill in the art.

As the wire 31 is payed out, its length is measured by a conventional transducer in the assembly 47. Such transducer produces an electrical signal on line 50 representing the wire being payed out and such signal is recorded in a conventional totalizer 60. The wire length is a rough approximation of the distance travelled by the boat 34 and reference electrode 32, and that distance, in accordance with the present invention, is correlated with the actual position of the boat which is monitored and indicated by conventional navigation equipment 61. More particularly, data designated distance markers (DM) are entered into the data stream of the computer 53 at intervals set by a pulse triggered by a conventional counter 62. More particularly, the totalizer 60 may produce a series of pulses or other information sequentially to the counter 62 which counts a pre-set number of pulses and then delivers a DM to the computer 53 after which the counter resets itself and commenses another counting cycle. The computer correlates the roughly approximated distance data with the potential difference data so that a real time pipeline potential graph based on the distance marks (DM) may be plotted by the plotter 56 and/or displayed by the display 55 and stored for subsequent analysis, operation, and/or display via the disc drive 54.

Each time the pre-set count set in the counter 62 occurs, a distance marker (DM) pulse is fed into the data stream delivered to the computer 53 for storage; a signal is also sent via line 63 to the navigation equipment 61 triggering the latter to produce an accurate fix of the position of the boat; and the counter 62 resets itself to commence counting for the next interval at which the next distance mark will occur. Such accurate fix of position may be taken manually or automatically depending on the navigation equipment 61.

Preferably the accurate position fix is made with respect to a chart in, for example, X-Y coordinates, on which the location of the pipeline is shown accurately. Therefore, since the position of the pipeline 10 is known in such coordinates system, the actual down line (down line meaning the location along the pipeline away from the area of the pipeline at which the connection 43 was made, this connection being at either end of or at any other test station along the pipeline) distances at each fix can be accurately determined. The actual down line distances, then, are correlated with the corresponding distance marks in the data stream to produce an accurate pipe-to-electrolyte electrical potential profile with respect to distance. Thus, although the field plots made by the plotter 56, for example, will show potential difference versus wire distance, the final plots producible in accordance with the invention will display such electrical potential difference versus real distance or down line distance.

According to the best mode of the present invention, the roughly approximated distance information correlated with the potential difference measurement information is stored on a floppy disc by the disc drive 54. After the survey has been completed, such data or information is correlated with the navigation data manually stored or automatically stored by the navigation equipment 61. After processing of such data to tabulate the values of potentials with respect to the corrected distance information a graph may be plotted out by conventional equipment, not shown, or may be manually plotted, to display the various potential difference values occurring at the corrected distance locations along the pipeline.

It will be appreciated that the computer 54 may be operated in a relatively conventional manner according to program control causing operation of the electrical equipment 36 in the above-described manner. The actual computer program language will, of course, depend on the particular computer employed. Nevertheless, a person having ordinary skill in the art would be able to draw up in conventional manner appropriate computer program input for the computer to effect the foregoing.

In the course of developing the invention, a pipeline, or portions of a pipeline, were surveyed using the above-described method and apparatus with the electrical equipment, in one instance, located in a conventional boat and, in another instance, with such equipment being located in a helicopter flying above the water along the pipeline. Thus, as used herein, the word boat represents any vessel capable of traversing across, or under, water, an aircraft, etc.

It also will be appreciated that a conventional electric meter, such as a high impedance voltmeter, may be connected in the electrical apparatus 36, for example across the inputs of the impedance amplifier 51, to display the instantaneous potential difference information prior to any conversion thereof which may occur in the A/D 52, computer 53, and/or peripheral equipment associated with the latter. Furthermore, potential difference information may be recorded manually as well as automatically with the remaining above described procedures in accordance with the method of the invention being followed using such manually taken data.

The navigation equipment 61 assures relatively accurate tracking of the pipeline to maintain the boat 34 substantially directly above the pipeline with the reference electrode 32 also being drawn substantially directly above the pipeline. Tracking of shorter pipelines may be accomplished using a Decca Trisponder System which employs two remote stations positioned on platforms and one mobile station on board the survey boat 34. Computerized equipment on the boat measures the distance between the mobile station and each of the remote stations, and by triangulation determines the position of the boat with respect to the coordinate grid or chart used in a particular area. The accuracy of such navigation system is approximately plus or minus three meters under ideal conditions. Alternatively, tracking of relatively long pipelines may be accomplished using a Decca Survey Pulse 8 System, which is a range-range/hyperbolic system. The latter system employs two permanent remote stations located in land and a mobile station located on the boat, and the accuracy of this system under ideal conditions has been found to be approximately fifteen meters. Moreover, in accordance with the preferred embodiment and best mode of the invention, when the survey is in progress, the navigation equipment 61 is automatically signalled at the pre-set wire intervals set in the counter 62, and the X-Y coordinates corresponding to those wire intervals are marked on the appropriate chart. Such coordinates may then be used to calculate the actual down line distance for use in plotting the final output graphs.

For the above-described reasons, it may be desirable to include insulated members or flanges in the pipeline risers 23, 25 (FIG. 1). The apparatus 30 may be used to examine or to test the effectiveness of such insulated flanges. To conduct such a test or examination, structure-to-electrolyte potential measurements may be made using the apparatus 30 with the connection 43 of the wire 31 to the riser 23 first on the platform side of the insulating flange 22 and then with such connection 43 being made on the pipeline side of the insulating flange. The measurements may be taken using a silver-silver chloride reference electrode 32 which remains approximately in the same position for both potential measurements. If the insulating flange 22 is effective, there will be a difference in the measured potentials in almost all cases. However, if the insulating flange is short circuited, both potential measurements will be at least approximately the same. It is possible that there will be no difference in the potential measurements even if the insulating flange is effectively insulating, but such a condition is a rarity. Summarizing, then, a difference in the measured potentials indicates effective insulation by the insulating flange 22 and no difference indicates a high probability of lack of insulating effectiveness.

According to the standards of the National Association of Corrosion Engineers, a negative (cathodic) voltage of at least 0.85 volts should be measured between a pipeline surface and a saturated copper-copper sulfate reference electrode contacting the electrolyte, in this case soil, for such an electrode is used in connection with onshore surveys, to assure effective cathodic protection. Moreover, when using a silver-silver chloride reference electrode, which usually is employed for offshore surveys in sea water, the negative voltage should be 0.80 volts to confirm effective cathodic protection of a submerged pipeline.

In accordance with the present invention consideration is given not only to the attainment of the minus 0.80 volts to a silver-silver chloride reference electrode measured between the pipeline surface and the electrolyte, but also consideration is given to the voltage (IR) drops that occur at areas other than drops resulting from contact resistance, wire resistance and resistance in the reference electrode itself. Such resistances and resulting IR drops can make the absolute value of the voltage V as read by a voltmeter 70 shown in FIG. 4 less than the absolute value of the pipe-to-electrolyte potential E. Such IR drops in the measuring circuit, though, may be compensated for by using an extremely high input impedance in the electrical equipment 36, and that is the reason for inserting the high impedance amplifier 51 in the apparatus illustrated in FIG. 3.

However, it has been found that the high input impedance amplifier and/or other high input impedance instrumentation included in the equipment 36, cannot satisfactorily compensate or eliminate IR drops which are an intrinsic part of the value of pipe-to-electrolyte potential E.

Figure 4:
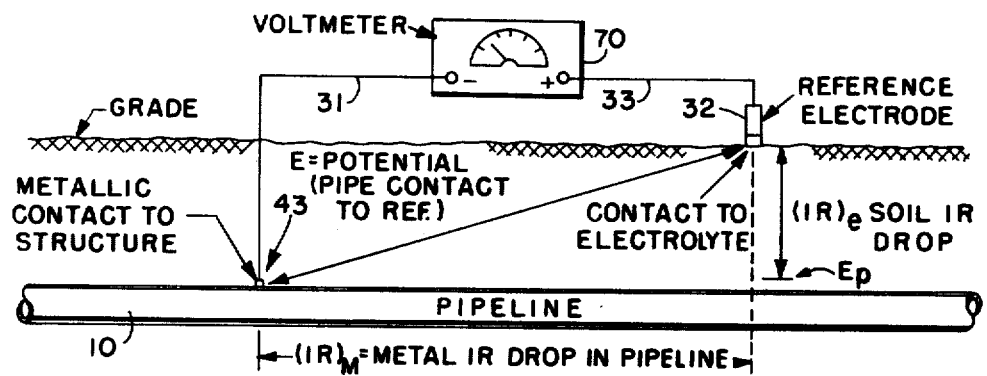
FIG. 4 is a schematic illustration depicting those voltage or potential drops encountered in electric potential surveys of buried structures.

The major components of such pipe-to-electrolyte potential E, as is shown particularly in FIG. 4, conformed to the following equation:

$$E = E_p + (IR)_M + (IR)_e \qquad \text{Eq. 1}$$

Whereas: $E_p$ = the pipe-to-electrolyte potential which exists between a hypothetical reference electrode immediately adjacent to the pipe surface and a metallic contact to the pipe close to the reference electrode; $(IR)_e$ = Voltage (IR) drop in the electrolyte between the hypothetical reference electrode placed immediately adjacent to the pipe surface and the actual position of the reference electrode within the electrolyte; and $(IR)_M$ = Voltage (IR) drop in pipe (often referred to as metal IR drop between a point of metallic contact close to the reference electrode and the actual point of contact to the pipeline structure.

In equation 1 there are two IR drops to consider, namely the metal drop in the pipeline $(IR)_M$ and the voltage gradient in the electrolyte $(IR)_e$. In onshore survey work the metal drop often is overlooked because the point of contact to the pipeline usually is relatively close to the placement of the reference electrode. However, the metal drop $(IR)_M$ is significant whenever there is line current on the pipeline and must be considered in the interpretation of potential measurements in such circumstances; this also is the case when the reference electrode is placed at rather large distances from the point of contact (connection 43 in FIG. 1), which is the usual occurrence in offshore surveys.

Figure 5:
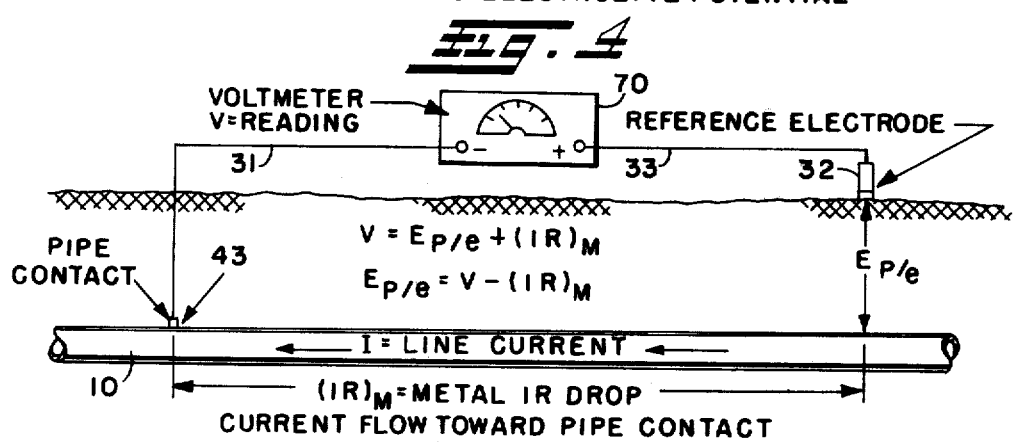
FIGS. 5 and 6 are schematic illustrations similar to that of FIG. 4 but also showing the interaction of line current.
Figure 6:
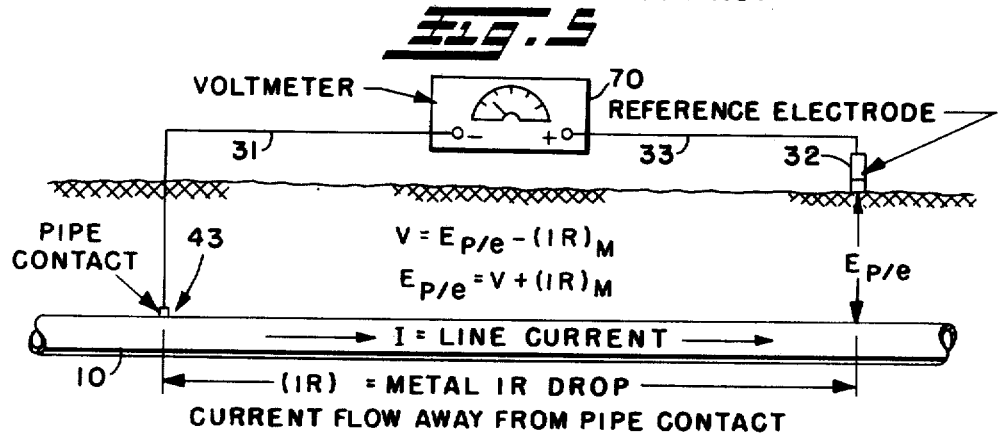

Thus, the line current results in a voltage drop between the point of contact (connection 43) and the position of the reference electrode 32 along the pipeline, and such voltage drop would be included in the voltage V measured on the voltmeter 70 of FIG. 4. Referring to FIGS. 5 and 6, then, in order to determine the actual pipe-to-electrolyte potential $E_{p/e}$, the metal drop $(IR)_M$ component must be added to or substracted from the measured voltage V. If line current flow on the pipeline is from the reference electrode location toward the connection 43, as is shown in FIG. 5, the actual pipe-to-soil potential $E_{p/e}$ will be less negative than the reading on the voltmeter V by the amount of the voltage drop in the line. Conversely, if the direction of line current is from the connection 43 toward the reference electrode 32 location, as is shown in FIG. 6, the actual pipe-to-soil potential $E_{p/e}$ will be more negative than the voltage reading V on the voltmeter 70 by the amount of voltage drop in the pipeline.

Applicants have discovered that, to detect the presence of line current, and to compensate for the resultant metal drop $(IR)_M$, complete potential profiles should be provided in both directions; the survey to obtain one profile being made with the connection 43 at one end of the pipeline and the survey to obtain the second profile being made with the connection 43 at the other end of the pipeline. If the two profiles thus taken are essentially the same, then the influence of line current may be discounted.

However, if a voltage drop between the two profiles is found, then the line current may be calculated according to the following formula:

$$\text{Metal drop } (IR)_M = I_L \times (0.252)/W$$

where metal IR drop = millivolts per 1000 feet;
$I_L$ = line current in milliamperes; and
W = weight of pipe in pounds per foot.

The latter and the constant 0.252 take into account the resistivity of a given type of pipe.

Although metal drop $(IR)_M$ is often overlooked in onshore survey work, considerable emphasis is placed by the National Association of Corrosion Engineers on considering soil or electrolyte drop $(IR)_e$ in taking measurements on onshore pipelines (particularly those comprised of uncoated pipes in relatively high resistivity soils). Nevertheless, general industry practice has been to disregard electrolyte drop $(IR)_e$ in electrolytes of which the resistivity is less than 1,000 ohm-cms. The resistivity of seawater is much less than the stated value and usually is approximately 30 ohm-cms; therefore, applicants treat in accordance with the present invention an offshore pipeline which may be buried beneath the ocean floor to be contained in an electrolyte of very low resistivity. Moreover, applicants have discovered that the actual placement of the electrode 32 with respect to the pipeline, as long as such placement is within the general vicinity of the pipeline, will not affect the potential profile obtained in accordance with the invention. Thus, the electrode 32 may be located to either side of the pipeline or at varying distances above the pipeline. The exact geometric position of the reference electrode 32 in the water with respect to the pipeline is not critical. Preferably, though, for optimum results the potential measurements should be taken with the reference electrode placed at the "electrical boundary" of the corrosion cell which customarily has been defined as a distance of from about 4 to about 6 pipe diameters from the pipe. However, applicants also have discovered that the potential may be taken relatively accurately with a reference electrode located in the water above the pipeline even though such location is beyond the so-called "electrical boundary".

Figures 7, 8:
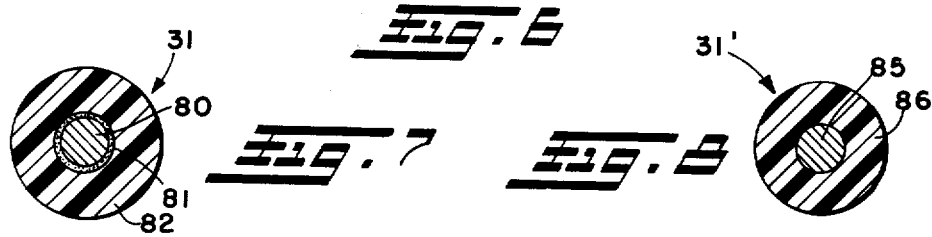
FIGS. 7 and 8 are schematic illustrations of insulated wires in accordance with the invention.

Turning now briefly to FIG. 7, a wire 31 made in accordance with the best mode and preferred embodiment of the invention is illustrated. Such wire 31 includes an electrical conductor 80 of elongate, relatively flexible material, such as copper. In fact, such wire 80 may be a 26 AWG copper magnet wire, although other gauge or materials also may be used, depending on the desired strength, weight, resistivity, conductivity, etc. parameters desired.

Preferably the wire 80 is coated with multiple layers of insulating material. The first coating or layer preferably is a varnish type material such as heavy armor polythermalese (HAPT) or formvar. Such coating increases the diameter of the insulated wire by about 2 mils. Such varnish coating may be applied in a conventional manner.

The second coating layer preferably is a polymer or copolymer material applied over the HAPT. In accordance with the preferred embodiment and best mode of the invention, such second coat or layer 82 is applied over the first layer 81 and is formed of approximately 8 mils thickness of ethylene propylene copolymer (E.P.C.), or a suitable thickness of an insulation which provides adequate electrical properties relative to the survey procedure. These properties include dielectric constant and volume resistivity. Such copolymer material preferably is applied using conventional extruder techniques with the result that the diameter of the insulated wire is increased by an additional 16 mils. After the extrusion process, the insulated wire may be dry sparked to test for holidays in the insulation. Any defects found in the insulation, then, may be repaired with Teflon tape and the wire then retested. The satisfactorily tested wire may be wound on 16 inch spools with 90,000 ft. per spool; and each spool preferably is equipped with a pigtail attached to the end of the wire at the hub of the spool in the manner illustrated generally in FIG. 2 of the application.

In the embodiment illustrated in FIG. 8, an alternate wire 31' is shown. Such wire may be, for example, of 29 AWG copperweld material 85 with no film or varnish coating, such as the coating 81 mentioned above, thereon. Rather, the only insulation on the wire is the 8 mil thick E.P.C. insulation 86 put on by extrusion. The thusly formed wire may be wet and dry sparked for testing. Any holidays found may be repaired using Teflon tape. The wire may be then wound on reels as described above.

Turning back to FIG. 3, the transducer in the wire dispenser and transducer in the preferred embodiment produces a pulse signal at one foot or other intervals. The totalizer 60 may be a conventional digital counter with a display that keeps a continuous count representing the length of wire spooled out or payed out during a survey run. The pre-set counter 62 may be a conventional device which is adjustable to a specified distance, such as 500 feet, 1000 feet, etc. prior to commencing a survey. Each time the pre-set distance or length of wire 31 has been payed out, the distance marker pulse is delivered by the counter 62 to the computer 53 and to the navigation equipment 61, as aforesaid. The sampling rate at which potential difference information is sensed or read by the computer 53 also may be adjusted or set in the computer prior to commencing a survey. The sampling rate is a function of time; therefore, the number of potential difference measurements made over a distance along the structure will be a function of the velocity of the survey vessel. The distance marker (DM) intervals are a function of the length of wire payed out from the wire dispenser and transducer 47, and, thus the time between distance marks is a function of survey vessel speed. An exemplary transducer for producing such pulses may be a Durant transducer which translates each turn of the pulley 44 (one foot) into an electrical signal.

The data stored on the floppy disc by the disc drive 54 may be analyzed and corrected in the manner described above either in the computer 53, if the latter has adequate capacity, or in further conventional computer equipment, which may be located, for example, at an onshore facility. At such facility, then, a plot could be prepared to display a complete accurate pipe-to-electrolyte potential difference profile.

To further improve the accuracy of the data obtained, corrected, and printed out in accordance with the present invention, a real time clock 90 (FIG. 3) may be added to feed time information to the computer 53. With exact time information known, calculation of exact position of the boat upon insertion of a distance marker, for example, can take into account the electric and magnetic effects of the earth where and when those effects are encountered. A further informational dimension also may be added in accordance with the invention by feeding to the computer 53 information concerning the depth of the reference electrode 32. Such depth information may be provided by a pressure sensitive transducer 91 connected to provide to the computer an electrical signal indicative of the electrode depth.

STATEMENT OF INDUSTRIAL APPLICATION

In view of the foregoing, it will be appreciated that the present invention provides method and apparatus for surveying structures in an electrolyte.

We claim:

1. A method of surveying a structure in an electrolyte, comprising moving a sensing means along the structure by means of a transporting means, sensing at locations along the structure the electrical potential difference between the structure and the electrolyte, measuring the approximate distances along the structure of a plurality of such locations relative to at least one of a reference position and a preceding such location to obtain information of the approximate position along the structure at which respective sensing steps are performed, making an accurate measurement of distance along the structure of at least one of such sensing means and such transporting means relative to at least one of a reference position and a preceding location, and correcting such approximate distances based on information from such accurate distance measurements.

2. The method of claim 1, said sensing comprising connecting wire to such structure and placing an electrode in contact with such electrolyte at locations along such structure and sensing potential difference between such structure via the wire and such electrode.

3. The method of claim 2, further comprising transporting a supply of such wire along such structure while paying out wire.

4. The method of claims 2 or 3, said measuring comprising measuring the length of such wire.

5. The method of claim 4, said making comprising using navigation equipment to measure accurate locations with respect to reference positions.

6. The method of claim 5, further comprising causing said navigation equipment to make an accurate measurement of distance at intervals determined by selected lengths of wire payed out.

7. The method of claim 1, further comprising determining whether the structure is carrying line current, and when the structure is carrying line current correcting such electrical potential difference information obtained in said sensing step based on such line current.

8. The method of claim 1, said sensing step being carried out while traversing the structure in one direction, and further comprising repeating said sensing step to detect whether the structure was carrying line current during said sensing steps.

9. The methods of claim 1, 2 or 3, such structure comprising a pipeline and such electrolyte comprising sea water and/or sea bottom, said sensing step comprising using a boat, submarine vehicle, or aircraft to pull a reference electrode through the sea water in proximity to the pipeline and to carry a supply of wire, one end of which is attached to a test station electrically connected to the pipeline, and equipment for conducting said sensing, measuring and making steps.

10. The method of claim 1, said making comprising using navigation equipment to determine accurate position information at intervals of predetermined distances measured during said measuring step.

11. The method of claim 1, said sensing comprising using a relatively light weight wire which is relatively economically disposable to connect with the structure and upon completion of the survey leaving the wire for disposal.

12. The method of claim 1, further comprising measuring and recording the time during which the survey is made.

13. The method of claim 2, wherein such electrolyte comprises sea water and/or sea bottom and such structure comprises a pipeline, and further comprising measuring and recording the height at which the electrode is located in such sea water above sea bottom during the survey.

14. The method of claim 1, further comprising storing the potential difference information as a function of the distance information.

15. The method of claim 1, further comprising displaying the potential difference information as a function of the distance information.

16. The method of claims 14 or 15, wherein such distance information is such approximate distances.

17. The method of claim 15, said displaying comprising displaying using a real time plotter.

18. The method of claim 15, said displaying comprising displaying using a cathode ray tube.

19. The method of claim 14, said storing comprising using a disc drive or tape drive.

20. The method of claim 1, said sensing comprising sensing at intervals determined as a function of such approximate distances.

21. The method of claim 1, said correcting comprising using a computer to effect such correction.

22. Apparatus for surveying a structure in an electrolyte, comprising sensing means for sensing at locations along the structure the electrical potential difference between the structure and the electrolyte, measuring means for measuring the approximate distances along the structure of a plurality of such locations relative to at least one of a reference position and a preceding such location to obtain information of the approximate position along the structure at which potential difference sensing has occurred, accurate measuring means for making an accurate measurement of distance along the structure of at least one of said sensing means and said measuring means relative to at least one of a reference position and a preceding location, and correcting means for correcting such approximate distances based on information from such accurate distance measurements.

23. The apparatus of claim 22, said sensing means comprising an adjustable impedance amplifier for compensating for relatively minor IR drop inaccuracies.

24. The apparatus of claim 22, said sensing means comprising a high impedance amplifier.

25. The apparatus of claim 22, further comprising a wire connected to such structure and an electrode in contact with such electrolyte, and said sensing means being connected to sense the potential difference between said wire and said electrode.

26. The apparatus of claim 25, said measuring means comprising means for measuring the length of wire payed out from a supply of wire moved along the structure.

27. The apparatus of claim 26, further comprising transducer means for producing signal information representative of predetermined lengths of wire payed out from said supply.

28. The apparatus of claim 25, further comprising means for causing said sensing means to sense electrical potential difference information in response to time.

29. The apparatus of claim 27, further comprising totalizer means for totalling information produced by said transducer means to indicate the length of wire payed out.

30. The apparatus of claim 29, further comprising control means for causing said accurate measuring means to make an accurate measurement in response to information from said totalizer representing a predetermined length of wire payed out.

31. The apparatus of claim 22, further comprising control means for causing said accurate measuring means to make an accurate measurement in response to the measurement of predetermined interval distances being measured by said measuring means.

32. The apparatus of claims 30 or 31, said control means comprising a counter and means for pre-setting the same to a predetermined count representative of a predetermined distance interval at which accurate measurements are to be made.

33. The apparatus of claims 30 or 31, said accurate measuring means comprising navigation equipment called into operation to measure accurate position in response to said control means.

34. The apparatus of claim 22, said accurate measuring means comprising navigation equipment called into operation to measure accurate position in response to measurement of predetermined distance intervals by said measuring means.

35. The apparatus of claim 22, said correcting means comprising a computer.

36. The apparatus of claim 22, said sensing means comprising analog to digital means for converting potential difference values to digital information.

37. The apparatus of claim 36, further comprising computer means for reading such digital information from said analog to digital means.

38. The apparatus of claim 22, further comprising display means for displaying the electrical potential difference information as a function of distance.

39. The apparatus of claim 38, said display means comprising a real time plotter.

40. The apparatus of claim 38, said display means comprising a cathode ray tube.

41. The apparatus of claim 22, further comprising storage means for storing the electrical potential difference information as a function of distance.

42. The apparatus of claim 41, said storage means comprising a disc drive or tape drive.

43. The apparatus of claims 38 or 41, wherein such distance is such approximate distance.

44. The apparatus of claims 22, 38 or 41, further comprising clock means for measuring time and means for storing the time of the survey.

45. The apparatus of claims 22, 38 or 41 wherein such structure is a pipeline and such electrolyte is sea water and/or sea bottom, said sensing means comprising an electrode in said sea water, and further comprising depth transducer means for sensing the depth of said electrode and means for recording such depth information.

46. The apparatus of claim 22, further comprising a wire for connecting said sensing means to said structure.

47. The apparatus of claim 46, said wire comprising an elongate conductor and an insulating coating of polymer material.

48. The apparatus of claim 47, said wire further comprising an insulating coating of film-like material between said polymer coating and said conductor.

49. The apparatus of claim 46, said wire comprising a relatively light weight wire which is relatively economically disposable, said wire having a flexibility allowing for facile handling and having adequate strength to prevent breakage when payed out over relatively long distances encountered in offshore surveys.

* * * * *